United States Patent [19]

Man

[11] Patent Number: Plant 7,162

[45] Date of Patent: Feb. 20, 1990

[54] BEGONIA PLANT NAMED CAMELLA

[75] Inventor: Jan Man, Lisse, Netherlands

[73] Assignee: Oglevee, Ltd., Connellsville, Pa.

[21] Appl. No.: 250,932

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

The new cultivar is generally characterized by its fullness of form and extensive branching. Flowers are clean in appearance. The plant is highly floriferous and the entire plant becomes covered with bloom. The new cultivar exhibits compact growth. The soft pink with a peach hue contrasts nicely with the foliage.

1 Drawing Sheet

BACKGROUND OF THE NEW PLANT

The present invewntion comprises a new and distinct cultivar of *Begonia*×*hiemalis* known by the varietal name of Camella. The new cultivar is a sport of the cultivar Petra (U.S. Plant Pat. Ser. No. 885,525). The new cultivar is larger in height and spread than the cultivar Petra. The soft pink with a peach hue of the flower differs from the orange with red overtone bloom of Petra.

The new cultivar was discovered March of 1985 at Limaplant b.v. in Lisse, Holland; was first asexually reproduced by cuttings at Limaplant b.v. in Lisse, Holland; and has been repeatedly asexually reproduced by cuttings for Oglevee Ltd. in Connellsville, Pa. It has been found to retain its distinctive characteristics through successive propagations.

The new cultivar is generally characterized by its fullness of form and extensive branching. Flowers are clean in appearance. The plant is highly floriferous and the entire plant becomes covered with bloom. The new cultivar exhibits compact growth. The soft pink with a peach hue contrasts nicely with the foliage.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 68° F. night and day. The plants were potted Feb. 2, 1988 in a peat-lite mix and fertilized with a 5 ppm mixture of 20N-10P-20K. Color readings were taken indoors under 200 foot-candles of cool white fluorescent tubes. Color references are to the R.H.S. Colour Chart of The Royal Horticultural Society of London, unless noted differently.

Botanical classification: *Begonia*×*hiemalis.*

Flower:

- *Fully expanded.*—5.5 in diameter; side view: flattened oval in appearance.
- *Borne.*—Compound dichasium (cyme).
- *Stems.*—Strong, medium compact, average stem width 1 to 2 cm.; color yellow -green group 144C.
- *Form.*—Semi-double to fully double. Each flower generally has 2 sepals, 6 petals, 4 to 8 petaloids (each group may vary±1 structure).
- *Permanence.*—Very long lasting bloom, average life span of 2 to 3 weeks.

Color:

- *Tonality from a distance.*—Soft pink with a peach hue.
- *Front of petals.*—Characterized overall by red group 48A.
- *Reverse of petals.*—Characterized overall by red group 49B.
- *Base of petals.*—Innermost base yellow-green group 154D.
- *Throat.*—None observed.
- *Discoloration.*—None.
- *Other comments.*—Large flower buds on very outside edge characterized by red group 50B. Center of outside of bud is yellow group 6D.

Petals:

- *Texture.*—Crepe paper like (gentle crinkles).
- *Appearance.*—Oval.
- *Arrangement.*—Semi-double to fully double.
- *Persistence.*—Very good flowers last a very long time up to 3 weeks and plant will continue to produce new buds.
- *Fragrance.*—None observed.

Reproductive organs: All reproductive organs have modified into petaloids. Anthers, filament, pollen, style and ovaries could not be observed.

Plant:

- *Form.*—Short compact internodes 3 cm. apart; good basal branching, strong stems give good support.
- *Growth.*—Very vigorous.
- *Height from soil line.*—18 to 20 cm. in 10 weeks (no pinch, no cycocel).
- *Spread.*—20 to 22 cm. in 11 weeks (no pinch, no cycocel).

Foliage:

*Size.*—Average length of 11 cm. and average width of 9 cm. on leaves 3 nodes up from base of stem.

*Quantity.*—Very abundant.

*Shape.*—Acute tip with irregularly lobed attachment; edge is slightly doubly serrate.

*Top side.*—Green group 139A.

*Underside.*—Green group 139B.

*Ribs and veins.*—Smooth on top side, raised on lower side, lower side veins only area on leaf where visible tricomes (hairs) appear.

*Rib and vein color.*—Top side: yellow-green group 145C; bottom: yellow-green group 146D.

*Margin.*—None.

*Stipules.*—None.

*Texture.*—Top: smooth, shiny and leathery; bottom: matt finish with raised veins.

I claim:

1. A new and distinct variety of Begonia characterized by fullness of form, extensive branching, soft pink with a peach hue and clean in appearance flowers and highly floriferous as shown and described herein and parts therefor.

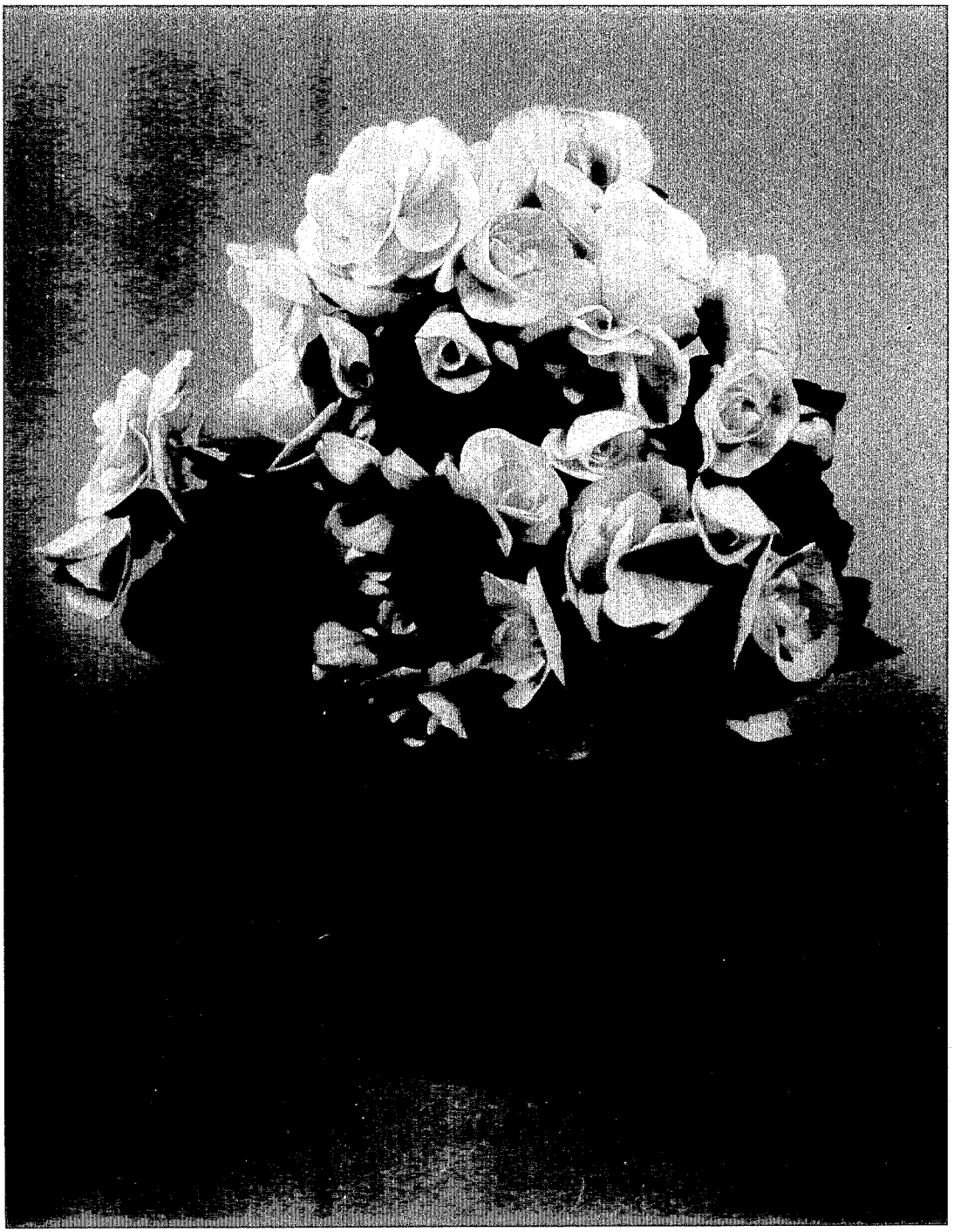

* * * * *